(12) United States Patent
Perkins

(10) Patent No.: US 10,175,109 B2
(45) Date of Patent: Jan. 8, 2019

(54) OPTICAL COMPUTING DEVICES AND METHODS UTILIZING MULTIPLE INTEGRATED COMPUTATIONAL ELEMENTS IN SEQUENCE

(71) Applicant: Halliburton Energy Services, Inc., Houston, TX (US)

(72) Inventor: David L. Perkins, The Woodlands, TX (US)

(73) Assignee: Halliburton Energy Services, Inc., Houston, TX (US)

(*) Notice: Subject to any disclaimer, the term of this patent is extended or adjusted under 35 U.S.C. 154(b) by 0 days.

(21) Appl. No.: 15/504,646

(22) PCT Filed: Sep. 16, 2015

(86) PCT No.: PCT/US2015/050474
§ 371 (c)(1),
(2) Date: Feb. 16, 2017

(87) PCT Pub. No.: WO2017/048251
PCT Pub. Date: Mar. 23, 2017

(65) Prior Publication Data
US 2017/0241839 A1    Aug. 24, 2017

(51) Int. Cl.
*G01J 3/02*    (2006.01)
*G01J 3/28*    (2006.01)
(Continued)

(52) U.S. Cl.
CPC ............ *G01J 3/2803* (2013.01); *G01J 3/02* (2013.01); *G01J 3/0256* (2013.01); *G01J 3/453* (2013.01);
(Continued)

(58) Field of Classification Search
None
See application file for complete search history.

(56) References Cited

U.S. PATENT DOCUMENTS 6,198,531 B1    3/2001    Myrick et al.
7,245,374 B2    7/2007    Hendriks
(Continued)

FOREIGN PATENT DOCUMENTS

WO    WO-2014/035421 A1    3/2014
WO    WO-2014/035422 A1    3/2014
(Continued)

OTHER PUBLICATIONS

International Search Report and Written Opinion from PCT/US2015/050474, dated May 18, 2016.

*Primary Examiner* — Shawn Decenzo
(74) *Attorney, Agent, or Firm* — Gilliam IP PLLC

(57) ABSTRACT

Detection sensitivity of optical computing devices may be improved by utilizing multiple integrated computational elements in combination with one another. Optical computing devices containing multiple integrated computational elements may comprise: two or more integrated computational elements that are identical to one another and optically interact sequentially with incident electromagnetic radiation, such that at least a portion of the photons from the incident electromagnetic radiation optically interacts with each integrated computational element; wherein the sequential optical interaction of the incident electromagnetic radiation with the two or more integrated computational elements increases a detection sensitivity of the optical computing device relative to that obtained when only one of the integrated computational elements is present; and a detector that receives the photons that have optically interacted with each integrated computational element.

18 Claims, 10 Drawing Sheets

(51) Int. Cl.
*G01J 3/453* (2006.01)
*G01N 21/31* (2006.01)

(52) U.S. Cl.
CPC ........ *G01N 21/31* (2013.01); *G01J 2003/283* (2013.01)

(56) References Cited

U.S. PATENT DOCUMENTS

| | | | |
|---|---|---|---|
| 7,405,825 B2 | 7/2008 | Schuurmans et al. | |
| 7,671,973 B2 | 3/2010 | Van Beek et al. | |
| 7,697,141 B2 | 4/2010 | Jones et al. | |
| 7,911,605 B2 | 3/2011 | Myrick et al. | |
| 7,920,258 B2 | 4/2011 | Myrick et al. | |
| 8,049,881 B2 | 11/2011 | Myrick et al. | |
| 8,154,726 B2 | 4/2012 | Blackburn et al. | |
| 8,208,147 B2 | 6/2012 | Myrick et al. | |
| 8,213,006 B2 | 7/2012 | Myrick et al. | |
| 8,237,920 B2 | 8/2012 | Jones et al. | |
| 8,240,189 B2 | 8/2012 | Myrick et al. | |
| 8,352,205 B2 | 1/2013 | Myrick et al. | |
| 8,358,414 B2 | 1/2013 | Csutak | |
| 8,379,199 B2 | 2/2013 | Freese et al. | |
| 8,525,995 B2 | 9/2013 | Jones et al. | |
| 8,575,541 B1 | 11/2013 | Jamison et al. | |
| 8,619,256 B1 | 12/2013 | Pelletier et al. | |
| 8,765,061 B2 | 7/2014 | Tunheim et al. | |
| 8,823,939 B2* | 9/2014 | Freese | G01N 21/17 356/433 |
| 8,879,053 B2* | 11/2014 | Freese | G01K 13/00 356/73 |
| 8,912,477 B2* | 12/2014 | Freese | G01N 21/17 250/206 |
| 8,960,294 B2* | 2/2015 | Freese | C09K 8/62 166/250.01 |
| 2007/0066877 A1 | 3/2007 | Arnold et al. | |
| 2009/0219539 A1 | 9/2009 | Myrick et al. | |
| 2010/0302539 A1 | 12/2010 | Myrick et al. | |
| 2013/0031964 A1 | 2/2013 | Tunheim et al. | |
| 2013/0031970 A1 | 2/2013 | Freese et al. | |
| 2013/0031971 A1 | 2/2013 | Freese et al. | |
| 2013/0031972 A1 | 2/2013 | Freese et al. | |
| 2013/0032333 A1 | 2/2013 | Freese et al. | |
| 2013/0032334 A1 | 2/2013 | Freese et al. | |
| 2013/0032338 A1 | 2/2013 | Kalia et al. | |
| 2013/0032339 A1 | 2/2013 | Kalia et al. | |
| 2013/0032340 A1 | 2/2013 | Freese et al. | |
| 2013/0032345 A1 | 2/2013 | Freese et al. | |
| 2013/0032736 A1 | 2/2013 | Tunheim et al. | |
| 2013/0033701 A1 | 2/2013 | Tunheim et al. | |
| 2013/0033702 A1 | 2/2013 | Tunheim et al. | |
| 2013/0034842 A1 | 2/2013 | Tunheim et al. | |
| 2013/0035262 A1 | 2/2013 | Freese et al. | |
| 2013/0162999 A1 | 6/2013 | Myrick et al. | |
| 2013/0284894 A1* | 10/2013 | Freese | G01N 21/17 250/208.2 |
| 2013/0284897 A1 | 10/2013 | Freese et al. | |
| 2013/0286398 A1 | 10/2013 | Freese et al. | |
| 2013/0286399 A1 | 10/2013 | Freese et al. | |
| 2013/0323484 A1 | 12/2013 | Pelletier et al. | |
| 2014/0061449 A1 | 3/2014 | Tunheim et al. | |
| 2014/0061513 A1 | 3/2014 | Tunheim et al. | |
| 2014/0067268 A1* | 3/2014 | Tunheim | G01M 3/22 702/2 |
| 2014/0076549 A1 | 3/2014 | Pelletier et al. | |
| 2014/0078499 A1 | 3/2014 | Tunheim et al. | |
| 2014/0080172 A1 | 3/2014 | Tunheim et al. | |
| 2014/0080223 A1 | 3/2014 | Tunheim et al. | |
| 2014/0081594 A1 | 3/2014 | Tunheim et al. | |
| 2014/0110105 A1 | 4/2014 | Jones et al. | |
| 2014/0118157 A1 | 5/2014 | Jamison | |
| 2014/0166361 A1 | 6/2014 | Jamison et al. | |
| 2014/0166871 A1 | 6/2014 | Jamison et al. | |
| 2014/0172177 A1 | 6/2014 | Jamison et al. | |
| 2014/0175271 A1 | 6/2014 | Samson et al. | |
| 2014/0252251 A1 | 9/2014 | Tunheim et al. | |
| 2014/0255598 A1 | 9/2014 | Simcock et al. | |
| 2014/0263974 A1 | 9/2014 | Freese et al. | |
| 2017/0370854 A1* | 12/2017 | Holden | G01N 21/31 |
| 2018/0017500 A1* | 1/2018 | Pelletier | G01N 21/3504 |

FOREIGN PATENT DOCUMENTS

| | | |
|---|---|---|
| WO | WO-2014/035423 A1 | 3/2014 |
| WO | WO-2014/035424 A1 | 3/2014 |
| WO | WO-2014/035425 A1 | 3/2014 |
| WO | WO-2014/035426 A1 | 3/2014 |
| WO | WO-2014/035427 A1 | 3/2014 |
| WO | WO-2014042642 A1 | 3/2014 |
| WO | WO-2014070648 A1 | 5/2014 |

* cited by examiner

OPTICAL COMPUTING DEVICES AND METHODS UTILIZING MULTIPLE INTEGRATED COMPUTATIONAL ELEMENTS IN SEQUENCE

BACKGROUND

The present disclosure generally relates to optical computing, and, more specifically, to optical computing devices and methods utilizing multiple integrated computational elements with increased detection sensitivity.

When making analytical measurements, sensitivity of the chosen analytical technique can often be problematic. As used in the analytical sciences and herein, the terms "sensitivity" or "detection sensitivity" can refer to two related factors: 1) the degree of change in analytical response that occurs per change in quantity of analyte, or 2) the minimum quantity of analyte that can be detected with a sufficient degree of confidence. The latter interpretation of "sensitivity" is also often referred to as the "detection limit." Low sensitivity analyses can sometimes fail to detect low abundance analytes, to determine if an analyte quantity is increasing or decreasing (e.g., due to a treatment, chemical reaction, or the like), or to differentiate between two or more samples having similar quantities of analyte. Analyses of samples containing complex mixtures of substances can be particularly problematic when the chosen analytical technique has a low sensitivity.

Although analytical sensitivity can be a concern in a number of fields, oilfield operations, such as subterranean treatment operations, represent one instance where sensitive analyses can often be desirable. Subterranean treatment operations can include, without limitation, drilling operations, stimulation operations, production operations, remediation operations, and the like. Such subterranean treatment operations are generally conducted with a treatment fluid, which can contain a variety of components that may directly or indirectly affect the desired purpose of the treatment operation. As used herein, the terms "treat," "treatment," "treating," and grammatical equivalents thereof refer to any subterranean operation that uses a fluid in conjunction with achieving a desired function and/or for a desired purpose. Use of these terms does not imply any particular action by the treatment fluid or a component thereof, unless otherwise specified herein.

Subterranean treatment operations are often quite susceptible to small changes in the quantity of one or more components present in a treatment fluid used to carry out the treatment operation. For example, a treatment fluid component that is present in an out-of-range amount may result in failure of a treatment operation and/or damage to a subterranean formation. Either of these outcomes are undesirable and can lead to increased costs and delayed production. Low-sensitivity analyses can exacerbate these issues, either by failing to identify out-of-range components before issues occur and/or barring proactive control of a treatment operation from taking place. Similar issues can be encountered in other process settings.

Spectroscopic analyses are well known for their sensitivity and versatility for detecting a wide variety of substances. Most spectroscopic instruments are general purpose and are not configured to detect any one particular substance or class of substance. That is, post-acquisition analysis of a sample's spectrum is usually conducted to determine the quantity of a substance of interest that is present. In addition, involved and time-consuming sample processing may also be needed to analyze for a particular substance with a given degree of accuracy and sensitivity, and the sample processing procedures may often vary considerably depending upon the nature of the sample undergoing analysis. Although spectroscopic analyses can be routinely carried out under laboratory conditions, they are considerably more difficult to transition into less controlled environments, such as the oilfield and other process settings, particularly when no or limited sample processing can be performed.

Optical computing devices represent an alternative to conventional spectroscopic equipment and analyses. Optical computing devices utilize an integrated computational element (ICE), also referred to as an "ICE core," which is a processing element that is specifically designed to analyze for a given component or characteristic of interest in a sample upon optical interaction of electromagnetic radiation therewith. As used herein, the term "integrated computational element" will refer to an optical processing element containing a plurality of optical thin film layers formed from various materials whose indices of refraction and thicknesses may vary between each layer. The layer compositions, thicknesses, and ordering may be chosen, based upon calculations, to selectively transmit or reflect predetermined fractions of electromagnetic radiation at different wavelengths such that the integrated computational element is configured to substantially mimic a regression vector corresponding to a particular component or characteristic of interest in a sample. As used herein, the term "characteristic" will refer to a substance's concentration in a sample or a derived physical property for the sample. The transmission or reflection function of the integrated computational element may represent the regression vector for a characteristic of interest, and the transmission function may be weighted with respect to wavelength. Accordingly, upon optically interacting electromagnetic radiation with a sample and with an integrated computational element, the electromagnetic radiation changes in a known and specific way that may be representative of the characteristic's magnitude in the sample. Following receipt of the electromagnetic radiation by a detector, an output from the detector can be correlated to the characteristic of interest. Even though a complex mixture of substances may be present in a given sample, the integrated computational element may be able to distinguish and analyze for this substance based on its unique regression vector.

Optical computing devices may be advantageous compared to conventional spectroscopic techniques, since optical computing analyses may be conducted rapidly, often in real-time, with limited to no sample preparation involved. Rather than obtaining an optical spectrum, which may require further interpretation and deconvolution, the output of optical computing devices is a real number that is correlatable to a characteristic of interest. Optical computing devices are also much more rugged than conventional spectroscopic equipment and can be deployed in locales where spectroscopic analyses may otherwise be problematic. Accordingly, optical computing devices may often be desirable for analyzing complex mixtures in various process environments, such as those encountered in the oilfield industry. As a further advantage, optical computing devices can often provide high-sensitivity analyses for a variety of substances, although there remain instances where their analytical sensitivity may still be a limiting factor.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

The present disclosure generally relates to optical computing, and, more specifically, to optical computing devices and methods utilizing multiple integrated computational elements with increased detection sensitivity.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, optical computing devices containing an integrated computational element may provide a number of advantages over conventional spectroscopic techniques, not to mention wet chemical analyses. In this regard, integrated computational elements may be specifically designed to analyze for a particular characteristic of interest, even in samples containing a complex mixture of substances. Before further discussing how the sensitivity of optical computing devices may be enhanced according to the embodiments of the present disclosure, a brief discussion of illustrative integrated computational elements and optical computing devices is provided hereinafter.

Figure 1:
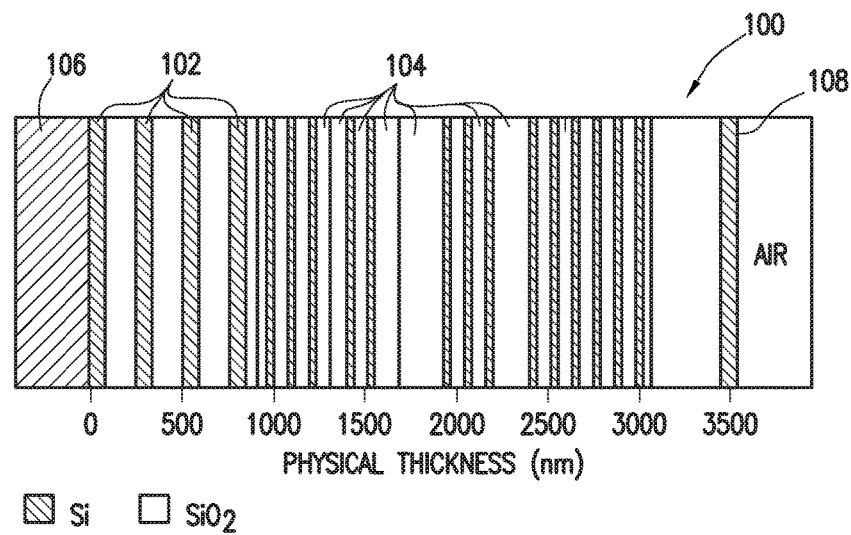
FIG. 1 is a diagram that illustrates an exemplary integrated computational element (ICE).

FIG. 1 is a diagram that illustrates an exemplary integrated computational element (ICE) 100. As illustrated, the ICE 100 may include a plurality of alternating layers 102 and 104, such as silicon (Si) and $SiO_2$ (quartz), respectively. In general, layers 102 and 104 consist of materials whose index of refraction is high and low, respectively. Other examples may include niobia and niobium, germanium and germania, MgF, $SiO_x$, and other high and low index materials known in the art.

Layers 102 and 104 may be strategically deposited on optical substrate 106, also referred to herein as a neutral optical element. As used herein, the term "neutral optical element" will refer to a substrate upon which layers 102 and 104 of an integrated computational element are deposited and which does not substantially optically interact with electromagnetic radiation over a wavelength range where the regression vector is being mimicked. That is, the neutral optical element provides mechanical support for layers 102 and 104 and exhibits a substantially flat or known optical profile, such as an optical transmission profile, in the wavelength range over which ICE 100 is operational. In some embodiments, optical substrate 106 may be BK-7 optical glass. In other embodiments, optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like. Although some of the materials that may comprise optical substrate 106 are among those that may comprise layers 102 and 104, the layer thicknesses when used as optical substrate 106 are much thicker. Opposite optical substrate 106, ICE 100 may include a layer 108 that is generally exposed to the environment of the device or the sample undergoing analysis. Layer 108 may comprise the same material or a different material than optical substrate 106.

It should be understood that exemplary ICE 100 is not intended to be predictive for any particular characteristic of interest, but is provided for purposes of illustration only. Consequently, when analyzing for a particular characteristic of interest, the number of layers 102 and 104, their composition and their thicknesses may vary. Moreover, the materials that make up each layer 102 and 104 (i.e., Si and $SiO_2$) may vary, depending on the application, cost of materials, and/or applicability of the materials to the monitored characteristic.

The number, thickness and composition, for example, of layers 102 and 104 may be determined by performing a conventional spectroscopic analysis and then mimicking the regression vector for determining a characteristic of interest by iteratively processing the various layer parameters to best reproduce or "best fit" the regression vector. A number of solutions may be obtained in this regard, and the various solutions may then be fabricated and further tested to determine if the ICE can provide a quality analysis of the characteristic of interest in practice. The regression vector being mimicked with ICE 100 typically includes any number of different wavelengths and may encompass one or more regions of the electromagnetic spectrum.

In some embodiments, the material of each layer 102 and 104 may be doped or two or more materials may be combined in a manner to achieve the desired optical performance. In addition to solids, exemplary ICE 100 may also contain liquids and/or gases, optionally in combination with solids, in order to produce a desired optical performance. In the case of gases and liquids, ICE 100 may contain a corresponding vessel (not shown), which houses the gases or liquids. Exemplary variations of ICE 100 may also include holographic optical elements, gratings, piezoelectrics, light pipe, digital light pipe (DLP), molecular factor devices, variable optical attenuators, frequency selective surface (FSS) elements, and/or acousto-optic elements, for example, that can create transmission, reflection, and/or absorptive properties of a material of interest.

The multiple layers 102 and 104 exhibit different refractive indices. By properly selecting the materials of layers 102 and 104, their relative thicknesses and spacing, ICE 100 may be configured to selectively transmit, reflect, or refract predetermined fractions of electromagnetic radiation at different wavelengths. Each wavelength is given a predetermined weighting or loading factor. The thickness and spacing of layers 102 and 104 may be determined using a variety of approximation methods from a spectrum of a substance of interest. These methods may include inverse Fourier transform (IFT) of the optical transmission spectrum and structuring ICE 100 as the physical representation of the IFT. The approximations convert the IFT into a structure based on known materials with constant refractive indices.

The weightings that layers 102 and 104 of ICE 100 apply at each wavelength are set to the regression weightings described with respect to a known equation, data, or spectral signature. Briefly, ICE 100 may be configured to perform the dot product of the input electromagnetic radiation into ICE 100 and a desired loaded regression vector represented by each layer 102 and 104 for each wavelength. As a result, the output intensity of the electromagnetic radiation from ICE 100 is related to the characteristic of interest.

As mentioned above, integrated computational elements may be specifically designed and fabricated based upon known spectroscopic factors. The number, composition, spacing and thicknesses of the various layers in an integrated computational element design may vary, and there may be a multiplicity of layer configurations or "best fit" solutions that may mimic the regression vector of a given characteristic with varying degrees of accuracy. Testing of a fabricated integrated computational element may determine how a given design performs in practice against other designs. Although they are intended to be predictive of the same characteristic, the "best fit" solutions for the integrated computational element designs may vary considerably in physical structure from one another depending upon the starting input parameters. Nevertheless, regardless of the "best fit" layer configuration in a finished integrated computational element design and its predictive capacity for determining a characteristic of interest, there is ordinarily no motivation to drastically change the number, spacing, arrangement, or composition of the layers. Doing so would be expected to change the spectral properties of the integrated computational element and likely degrade its predictive capacity for determining a characteristic of interest. That is, changing the layer configuration would be expected to alter the integrated computational element's regression vector for determining a characteristic of interest.

The present inventor surprisingly discovered that by sequentially interacting electromagnetic radiation with two or more integrated computational elements, significantly improved detection performance may be obtained in certain instances. Specifically, the inventor discovered that by optically interacting electromagnetic radiation with two or more identical integrated computation elements, where the integrated computational elements are identical in all respects, surprisingly increased detection sensitivity may be obtained for some integrated computational element designs. For example, in a suite of 20,000 integrated computational element designs, the sequential combination of two identical designs (i.e., same physical structure and regression vector) with one another produced a sensitivity increase of greater than 15% for at least about 4% of the designs. The optical interaction may involve transmitting the electromagnetic radiation sequentially through the integrated computational elements, by reflecting the electromagnetic radiation between integrated computational elements or any combination thereof.

Transmissive embodiments may be particularly advantageous. For transmissive embodiments, integrated computational element designs providing increased detection sensitivity upon configuration in serial fashion may often be those that transmit a high percentage of incident electromagnetic radiation through the integrated computational element from one side to the other. Upon transmitting the electromagnetic radiation through each integrated computational element, the amount of transmitted electromagnetic radiation is reduced for each integrated computational element added (e.g., at a wavelength where 50% transmission takes place, two identical integrated computational elements lower the incident electromagnetic radiation intensity by 75%). From an operational and efficiency standpoint, transmissive embodiments may be particularly desirable, since a stacked or monolithic combination of the integrated computational elements may be used in order to minimize space within the optical computing device and to provide for ready consolidation of the two or more integrated computational elements with one another. Other configurations are also possible, as discussed hereinbelow.

As indicated above, there would ordinarily be no motivation whatsoever to combine two or more integrated computational elements with one another, regardless of whether the integrated computational elements are the same or different. By combining a first integrated computational element with a second integrated computational element, one would not expect the combined layer configuration to remain predictive for the characteristic of interest, or at least one would likely expect the predictive capacity to decrease. In contrast to the expected behavior, the present inventor discovered that increased detection sensitivity may be obtained by sequentially interacting electromagnetic radiation with identical integrated computational elements for certain design configurations.

Although optical computing devices already may possess a number of distinct advantages over conventional spectroscopic equipment and techniques, these advantages may be further highlighted by enhancing their detection sensitivity. Enhanced detection sensitivity may make the integrated computational elements suitable for performing various analyses for which they might otherwise be unsuitable or provide less than desired performance. For example, by increasing the detection sensitivity of an optical computing device through configuring two or more identical integrated computational elements to optically interact sequentially with electromagnetic radiation, a greater degree of proactive or reactive process control may be realized in various applications, such as in the monitoring of various oilfield processes. Other illustrative industries in which similar benefits may be realized include, for example, environmental monitoring, medical testing, and other fields in which low abundance analytes are tested. In addition, from a design and fabrication standpoint, fewer integrated computational element designs may need to be computationally characterized and fabricated before obtaining a design with suitable performance for carrying out a particular analysis.

In addition to the foregoing benefits, optical computing devices may be configured to detect as many characteristics as desired for a given sample. All that is required to accomplish the monitoring of multiple characteristics is the incorporation of suitable integrated computational elements and detection means within the optical computing device for analyzing each characteristic. Since the properties of a sample may be a combination of the properties of the various substances therein, (e.g., a linear, non-linear, logarithmic, and/or exponential combination of the properties), the more characteristics that are detected and analyzed, the more accurately the properties of the sample can be determined. When multiple characteristics are being analyzed by a single optical computing device, each of the characteristics may be analyzed by using multiple integrated computational elements according to the embodiments of the present disclosure, or only those characteristics that benefit from increased detection sensitivity may utilize multiple integrated computational elements.

Chemical, mechanical or physical properties of a sample that may be detected using multiple integrated computational elements according to the present disclosure are not believed to be particularly limited. Illustrative characteristics that may be determined using multiple integrated computational elements include, for example, analyte concentrations, impurity content, viscosity, density, opacity, color, refractive index, liquid content, oxidation state, particle size, pH, salinity, total dissolved solids, ionic strength, porosity, bacteria content, combinations thereof, and the like.

Illustrative optical computing devices described herein contain two or more identical integrated computational elements. As used herein, the term "optical computing device" will refer to an optical device that is configured to receive an input of electromagnetic radiation from a sample and produce an output of electromagnetic radiation from a processing element that is diagnostic of a characteristic of the sample. The processing element may be an integrated computational element arranged within the optical computing device.

As used herein, the term "electromagnetic radiation" will refer to radio waves, microwave radiation, infrared and near-infrared radiation, visible light, ultraviolet light, X-ray radiation or gamma ray radiation. In more particular embodiments, the electromagnetic radiation may comprise near-infrared radiation in a wavelength range of about 1000 nm to about 5000 nm. The output of electromagnetic radiation from the processing element can be reflected electromagnetic radiation, transmitted electromagnetic radiation, and/or dispersed electromagnetic radiation. Whether reflected, transmitted, and/or dispersed electromagnetic radiation is analyzed by the detector may be dictated by the structural parameters of the optical computing device and other operational factors. Fluorescent, phosphorescent, or blackbody emissions and/or the like of the sample may be analyzed using the optical computing device, and in such embodiments, a source of electromagnetic radiation may be omitted. In some or other embodiments, the electromagnetic radiation may comprise fluorescence, luminescence, Raman scattering, Brillion scattering, and/or Raleigh scattering.

As used herein, the term "optically interact" and grammatical variations thereof will refer to the reflection, transmission, scattering, diffraction, or absorption of electromagnetic radiation on, through, or from one or more integrated computational elements. Accordingly, the term "optically interacted electromagnetic radiation" refers to electromagnetic radiation that has been reflected, transmitted, scattered, diffracted, or absorbed by, emitted, or re-radiated, for example, using the integrated computational elements.

In some embodiments, the sample being analyzed by the optical computing device may comprise a fluid. As used herein, the term "fluid" will refer to any substance that is capable of flowing, including particulate solids, liquids, gases, slurries, emulsions, powders, muds, glasses, any combination thereof, and the like. In some embodiments, the fluid can be an aqueous fluid, including water or the like. In some embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Fluids can include various flowable mixtures of solids, liquids and/or gases. Illustrative gases that can be considered fluids according to the present embodiments include, for example, air, nitrogen, carbon dioxide, argon, helium, hydrogen disulfide, mercaptan, thiophene, methane, ethane, butane, and other hydrocarbon gases, combinations thereof and/or the like.

In some or other embodiments, the sample being analyzed by the optical computing device may comprise a solid. Solids may include, for example, drill cuttings, wellbore surfaces, and the like.

As used herein, the term "sample" or other variants thereof will refer to at least a portion of a substance of interest to be analyzed using an optical computing device. The sample may be a fluid, such as those described above, or a solid such as, but not limited to, rock formations, concrete, and other solid surfaces. It is to be understood that a sample need not necessarily represent a discrete aliquot of a bulk material. Rather, sampling of a bulk material may take place through a sampling window, wherein the bulk material may be static or flowing during the analysis.

Accordingly, in various embodiments, optical computing devices of the present disclosure may comprise: two or more integrated computational elements that are identical to one another and optically interact sequentially with incident electromagnetic radiation comprising a plurality of photons, such that at least a portion of the photons from the incident electromagnetic radiation optically interact with each integrated computational element; wherein the sequential optical interaction of the incident electromagnetic radiation with the two or more integrated computational elements increases a detection sensitivity of the optical computing device relative to that obtained when only one of the integrated computational elements is present; and at least one detector that receives the photons that have optically interacted with each integrated computational element.

The electromagnetic radiation that optically interacts sequentially with the integrated computational element may be transmitted electromagnetic radiation, reflected electromagnetic radiation, scattered electromagnetic radiation, or any combination thereof. FIGS. 2-7 show diagrams that illustrate exemplary configurations of two or more integrated computational elements in an optical computing device, in which the integrated computational elements sequentially receive incident electromagnetic radiation from a source. Transmissive embodiments may be particularly desirable, such as those depicted in FIGS. 2-6.

Figure 3:
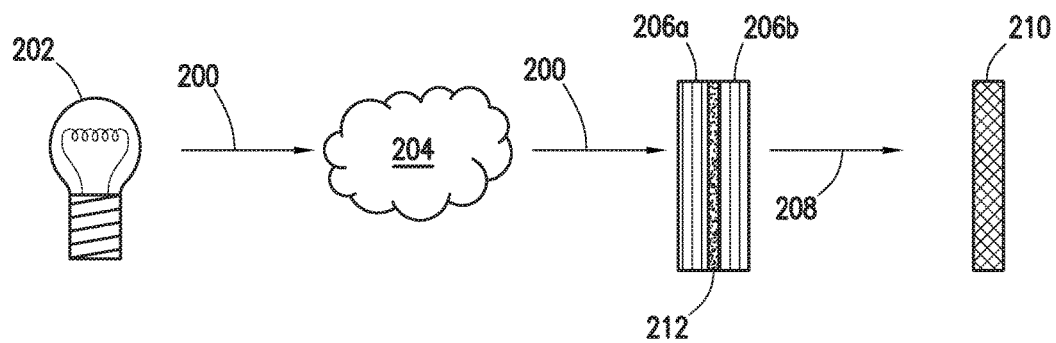
Figure 4:
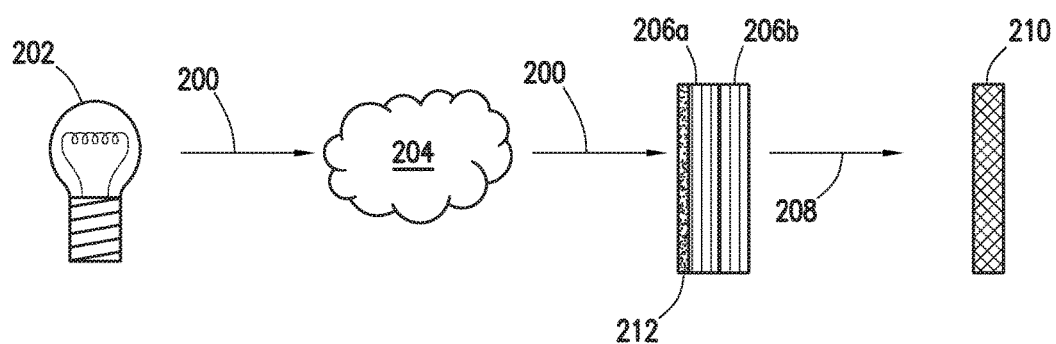
Figure 5:
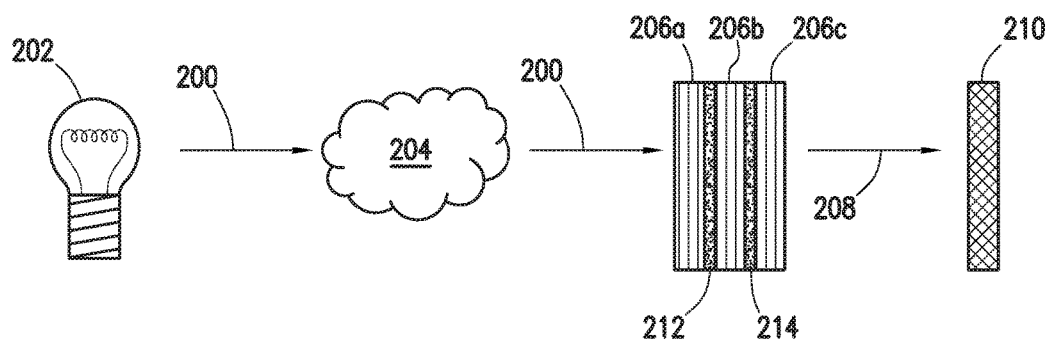

Although FIGS. 2-4, 6 and 7 have depicted only two integrated computational elements, it is to be recognized that greater numbers of these components may be present in some embodiments, such as the three integrated computational elements depicted in FIG. 5. Hence, it is to be recognized that greater than two or greater than three integrated computational elements may be disposed in sequence without departing from the scope of any of illustrative FIGS. 2-7. The ultimate number of integrated computational elements employed may be a function of the particular integrated computational element design and how well multiple integrated computational elements of that design may be sequenced to enhance the detection sensitivity. For example, if a particular integrated computational element design produces increased sensitivity with two integrated computational elements but decreased sensitivity with three integrated computational elements, two sequential integrated computational elements of that design may be the maximum for increasing detection sensitivity. In addition, optical computing device constraints and other factors may impact the ultimate number of integrated computational elements that may be combined in sequence with one another.

Accordingly, in some embodiments of the present disclosure, two integrated computational elements may be placed in sequence with one another in order to realize an increased detection sensitivity. In other embodiments, more than two integrated computational elements may be placed in sequence with one another in order to realize an increased detection sensitivity. For example, in some embodiments, three integrated computational elements, or four integrated computational elements, or five integrated computational elements, or six integrated computational elements, or seven integrated computational elements, or eight integrated computational elements, or nine integrated computational elements, or ten integrated computational elements may be placed in sequence with one another. Given the benefit of the present disclosure and straightforward testing or modeling of the sequenced integrated computational elements, one of ordinary skill in the art will be able to determine an appropriate number of integrated computational elements to place in sequence with one another to realize a desired sensitivity increase.

In some embodiments, the two or more integrated computational elements may be disposed in series with one another along a linear optical pathway. When disposed along a linear optical pathway, the incident electromagnetic radiation may optically interact by being transmitted through each of the integrated computational elements. That is, in such embodiments, photons from the incident electromagnetic radiation may pass through each of the integrated computational elements prior to reaching the detector. In the course of optically interacting with the integrated computational elements, the photons may be changed so as to be correlatable with a characteristic of a sample.

In some embodiments, the two or more integrated computational elements may comprise a monolithic structure. In such embodiments, the two or more integrated computational elements may be in contact with one another such that they are "stacked" or "consolidated" together. The integrated computational elements may be adhesively or mechanically attached to one another, although other means of adherence also reside within the scope of this disclosure. The stacking or consolidation may take place such that layer 108 from a first integrated computational element is adjacent to optical substrate 106 from a second integrated computational element. That is, the first and second integrated computational elements are placed head-to-tail with respect to one another in a monolithic structure, such that plural layers 102 and 104 from each integrated computational element are separated from one another by at least one neutral optical element.

Figure 2:
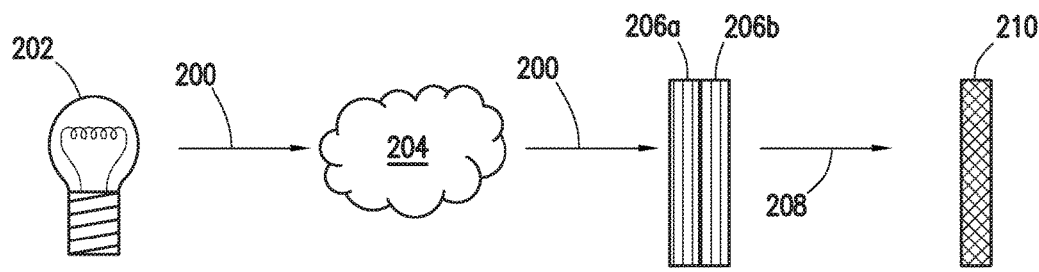
FIGS. 2-7 show diagrams that illustrate exemplary configurations of two or more integrated computational elements in an optical computing device, in which the integrated computational elements sequentially receive incident electromagnetic radiation from a source.

FIG. 2 shows a diagram that illustrates two integrated computational elements in an optical computing device, in which the integrated computational elements are sequenced in a monolithic structure. As depicted in FIG. 2, incident electromagnetic radiation 200 from source 202 optically interacts with sample 204 and integrated computational elements 206a and 206b, each of which has a structure similar to integrated computational element 100, described above. Source 202 may be any device capable of emitting or generating electromagnetic radiation, as defined herein. For example, source 202 may be a light bulb, a light emitting device (LED), a laser, a blackbody, a photonic crystal, an X-Ray source, a gamma ray source, combinations thereof, or the like. As a result of optically interacting with sample 204 and with integrated computational elements 206a and 206b in a head-to-tail fashion, optically interacted electromagnetic radiation 208 with differing properties from incident electromagnetic radiation 200 is produced. Optically interacted electromagnetic radiation 208 carries information about sample 204 in terms of the characteristic being analyzed. Upon receipt of optically interacted electromagnetic radiation 208 at detector 210, an output may be obtained that may be correlated with the analyzed characteristic of sample 204. While FIG. 2 shows the electromagnetic radiation 208 passing through sample 204, it is also contemplated herein to reflect electromagnetic radiation 208 off of sample 204, as discussed in further detail herein. Reflection may be desirable for translucent, opaque or solid samples, for example.

Detector 210 may comprise, but is not limited to, a thermal detector such as a thermopile or photoacoustic detector, a semiconductor detector, a piezo-electric detector, charge coupled device (CCD) detector, a video or array detector, a split detector, a photon detector (such as a photomultiplier tube), photodiodes, and/or combinations thereof, or the like. Other types of detectors will be familiar to one having ordinary skill in the art.

In monolithic integrated computational element structures, such as those depicted in FIG. 2, the two or more integrated computational elements may have a combined thickness ranging between about 10 nm and about 3000 nm, or between about 10 nm and about 1000 nm, or between about 1000 nm and about 3000 nm. In some embodiments, the integrated computational elements may have a combined thickness of up to about 5000 nm. The combined thickness may be dependent upon the number of layers and their individual thicknesses in each integrated computational element, and the number of integrated computational elements that are placed in sequence with one another.

A monolithic structure containing two or more integrated computational elements may comprise two or more integrated computational elements that are disposed on opposing sides of an additional neutral optical element. That is, in such embodiments, the additional neutral optical element may be interposed or sandwiched between each integrated computational element. Again, the integrated computational elements are disposed head-to-tail with respect to one another, with plural layers 102 and 104 being separated from one another by layer 108 of a first integrated computational element, neutral optical element 106 of a second integrated computational element, and the additional neutral optical element. FIG. 3 shows a diagram of two integrated computational elements in an optical computing device in which the integrated computational elements are separated by an additional neutral optical element. FIG. 3 is substantially similar to the configuration of FIG. 2 and like reference characters are used, except that additional neutral optical element 212 is interposed between integrated computational elements 206a and 206b. Use of additional neutral optical element 212 may be advantageous when it is desired to achieve increased spacing between integrated computational elements 206a and 206b.

Alternately, neutral optical element 212 may be shared between integrated computational elements 206a and 206b in a monolithic structure. That is, neutral optical element 212 may comprise layer 108 of a first integrated computational element and neutral optical element 106 of a second integrated computational element. In fabricating such monolithic combinations of neutral optical element 212 and integrated computational elements 206a and 206b, disposed on each side thereof, a first integrated computational element (e.g., integrated computational element 206a) may be deposited on a first side of neutral optical element 212 (e.g., by atomic layer deposition, chemical vapor deposition, or another suitable layer deposition technique). Thereafter, the neutral optical element can be flipped over, and a second integrated computational element (e.g., integrated computational element 206b) can be deposited on the opposing side of neutral optical element 212. The order of layer deposition in integrated computational element 206b is reversed from that of 206a in order to maintain the head-to-tail disposition of the two integrated computational elements.

Optionally, additional neutral optical element 212 may be positioned, such that integrated computational elements 206a and 206b are disposed on the same side of additional neutral optical element 212, as depicted in FIG. 4. That is, the monolithic combination of integrated computational elements depicted in FIG. 2, with the integrated computational elements disposed head-to-tail with respect to one another, may be further placed upon additional neutral optical element 212.

Although FIGS. 2-4 have depicted two integrated computational elements, in further illustrative configurations, additional integrated computational elements may be present. For example, additional integrated computational elements may be incorporated into the configuration of FIG. 2 by placing one or more integrated computational elements in a head-to-tail fashion into the monolithic structure of FIG. 2. Similarly, additional integrated computational elements may be incorporated into the monolithic configuration of FIG. 3 by placing one or more integrated computational elements in a head-to-tail fashion and another neutral optical element between each added integrated computational element. Such a configuration is depicted in FIG. 5, in which integrated computational elements 206a, 206b, and 206c are disposed in a head-to-tail fashion and are further separated by additional neutral optical elements 212 and 214.

Figure 6:
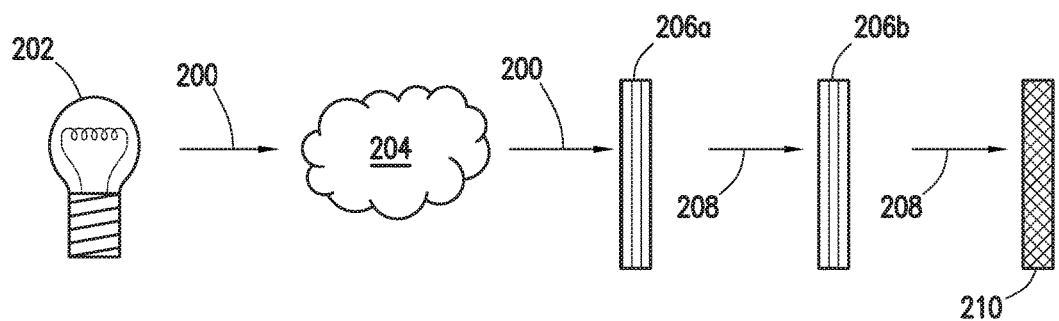

In still other embodiments, the two or more integrated computational elements may be disposed in series with one another along a linear optical pathway but spaced apart from one another. As in the monolithic structures described above, the integrated computational elements in spaced apart configurations are again disposed head-to-tail with respect to one another. FIG. 6 shows a diagram of two integrated computational elements in an optical computing device in which the integrated computational elements are spaced apart from one another in a linear optical pathway. The nominal separation distance between the integrated computational elements may range from microns to several feet or more depending on particular design constraints for the optical computing device.

Figure 7:
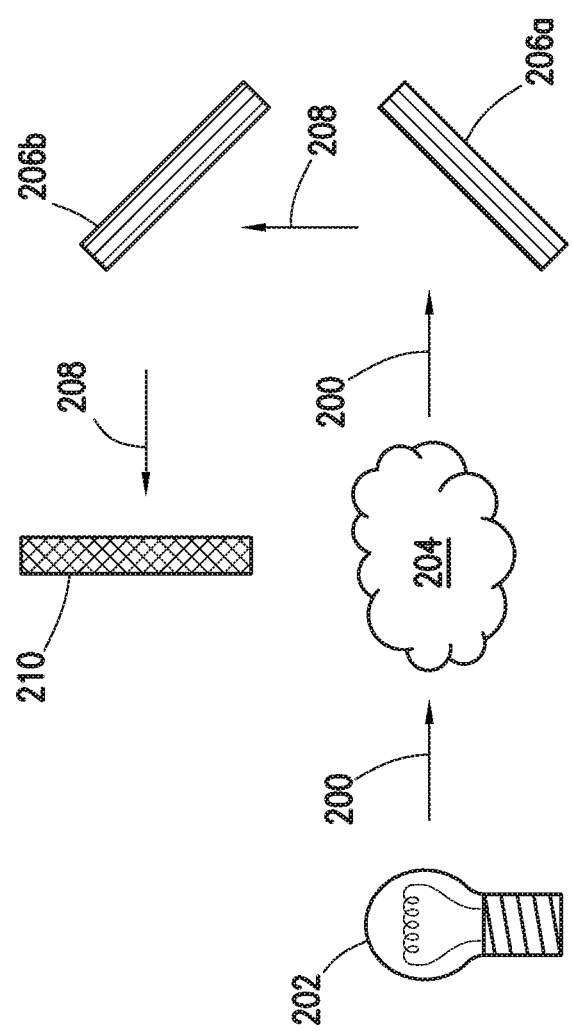

In the integrated computational element configurations depicted in FIGS. 2-6, the electromagnetic radiation reaching the detector is that transmitted through each of the integrated computational elements. In alternative embodiments, the electromagnetic radiation may comprise reflected electromagnetic radiation, such that the integrated computational elements may be disposed in a non-linear optical pathway while still optically interacting in sequence with incident electromagnetic radiation. As used herein, the term "non-linear optical pathway" will refer to an optical pathway that extends in at least two dimensions. In contrast, in a linear optical pathway, the electromagnetic radiation progresses in only one direction. FIG. 7 shows a diagram of two integrated computational elements in an optical computing device in which the integrated computational elements are located in sequence in a non-linear optical pathway. Again, integrated computational elements 206a and 206b are disposed head-to-tail with respect to one another along the non-linear optical pathway. The configuration of FIG. 7 differs from that of FIG. 6 in that incident electromagnetic radiation 200 is reflected from integrated computational elements 206a and 206b to produce optically interacted electromagnetic radiation 208, which ultimately reaches detector 210.

It is to be further recognized that combinations of transmissive and reflective configurations may be used in some embodiments. For example, incident electromagnetic radiation 200 may be reflected from integrated computational element 206a and optically interacted electromagnetic radiation 208 may be transmitted through integrated computational element 206b, or vice versa.

Moreover, when the integrated computational elements are spaced apart, as in FIGS. 6 and 7, monolithic integrated computational element structures, such as depicted in FIGS. 2-5, may be utilized at each spaced apart location, if desired.

Although FIGS. 2-7 have depicted a discrete source 202 of electromagnetic radiation, it is to be recognized that this feature may be optional in some embodiments. For example, in some embodiments, electromagnetic radiation may be emitted from sample 204 such that another source 202 of electromagnetic radiation is unnecessary. For example, in some embodiments, sample 204 may be radioactive or luminescent and therefore radiate electromagnetic radiation that optically interacts with the multiple integrated computational elements. In some or other embodiments, sample 204 may be a blackbody and/or emit radiation upon being perturbed mechanically, magnetically, electrically, chemically, or any combination thereof. Accordingly, embodiments are contemplated herein in which source 202 of electromagnetic radiation is omitted from a particular optical computing device.

Although FIGS. 2-7 have shown incident electromagnetic radiation 202 optically interacting with sample 204 before optically interacting with integrated computational elements 206a and 206b, incident electromagnetic radiation 202 may optionally optically interact with integrated computational elements 206a and 206b before optically interacting with sample 204. Although not possible with a monolithic structure, incident electromagnetic radiation 202 may optically interact first with integrated computational element 206a before optically interacting with sample 204 and then with integrated computational element 206b (i.e., in the configurations of FIGS. 6 and 7). That is, in some embodiments, sample 204 may be interposed between at least two of the integrated computational elements.

Although not specifically shown in FIGS. 2-7, one or more spectral elements may be employed in order to restrict the optical wavelengths and/or bandwidths of the electromagnetic radiation source and thereby eliminate unwanted electromagnetic radiation frequencies that are detrimental to and/or are of no importance in an analysis. Such spectral elements can be located anywhere along the optical train, but are typically employed directly after the electromagnetic radiation source, before the incident electromagnetic radiation optically interacts with the sample and the integrated computational elements. Spectral elements that may be present include, for example, choppers, collimators, bandpass filters, beam splitters, and the like.

Although FIGS. 2-7 have shown all of the incident electromagnetic radiation as either being transmitted through or reflected from the integrated computational elements, it is to be further recognized that a portion of the electromagnetic radiation may take an alternative optical pathway. For example, the electromagnetic radiation being transmitted through the integrated computational elements may be related to the characteristic of interest, and electromagnetic radiation not related to the characteristic of interest may be reflected from the integrated computational element, or vice versa. The electromagnetic radiation not related to the sample (i.e., reflected electromagnetic radiation in the case of the characteristic being related to transmitted electromagnetic radiation) may be received by a second detector and processed to produce a compensating signal. For example, the compensating signal obtained from the second detector may be representative of radiating deviations in the electromagnetic radiation source. Radiating deviations can include, for example, intensity fluctuations in the electromagnetic radiation, interferent fluctuations (e.g., dust or other interferents passing in front of the source of electromagnetic radiation), partially opaque films formed on the source of electromagnetic radiation, combinations thereof, or the like.

In some or other embodiments, a beam splitter (not shown) may be used to split the stream of electromagnetic radiation emanating from the source of electromagnetic radiation, such that the portion of the split electromagnetic radiation passing to the second detector does not optically interact with either of the integrated computational elements. Again, the electromagnetic radiation received at the second detector may be used to assess radiating deviations in the source of electromagnetic radiation or otherwise provide a compensating signal. Techniques for processing the compensating signal may include, for example, utilizing principal component analysis techniques employed with statistical analysis software packages such as, for example, XL Stat for MICROSOFT® EXCEL®, the UNSCRAMBLER® from CAMO Software, and MATLAB® from MATHWORKS®.

In some embodiments, the output of the detector can be fed into an algorithm operating under computer control. The algorithm may be configured to make predictions on how changes in the characteristic result in overall changes to the sample, particularly changes affected by simultaneous changes of multiple characteristics. In some embodiments, the algorithm can produce an output that is readable by an operator who can manually take appropriate action, if needed, based upon the output. In some embodiments, the algorithm can take proactive process control by automatically adjusting the characteristics of, for example, a treatment fluid being introduced into a subterranean formation or by halting the introduction of the treatment fluid in response to an out of range condition.

The algorithm can be part of an artificial neural network configured to use the characteristic and predict how to modify the sample in order to alter its properties in a desired way. The artificial neural network can be trained using samples having known concentrations, compositions, and/or properties, thereby generating a virtual library. As the virtual library available to the artificial neural network becomes larger, the neural network can become more capable of accurately predicting the characteristics of a sample having any number of analytes present therein.

It is to be recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected using the optical computing devices can be archived along with data associated with operational parameters being logged at a job site.

Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Figure 8:
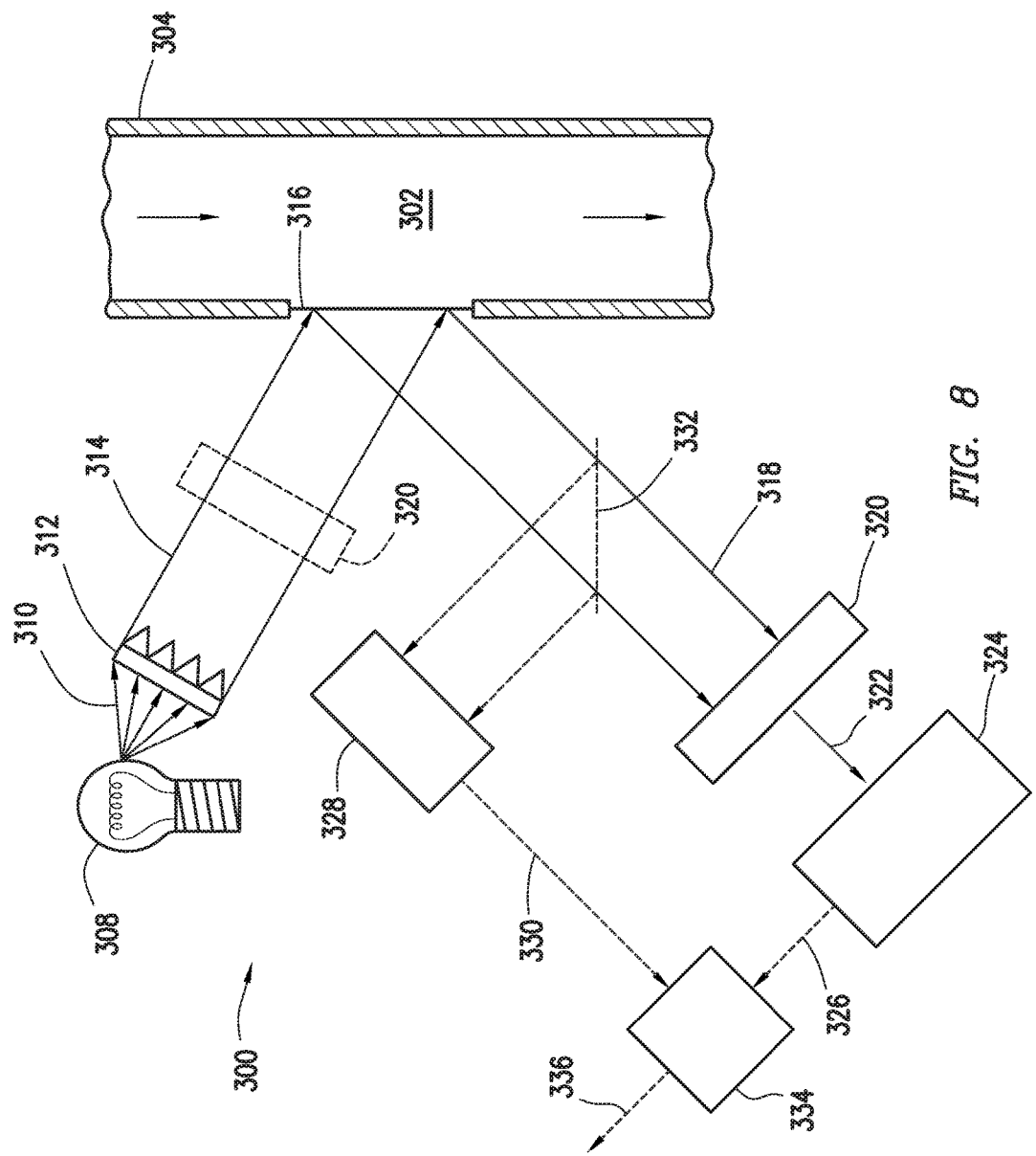
FIG. 8 shows a diagram that illustrates an exemplary optical computing device in which electromagnetic radiation is reflected from a fluid sample.
Figure 9:
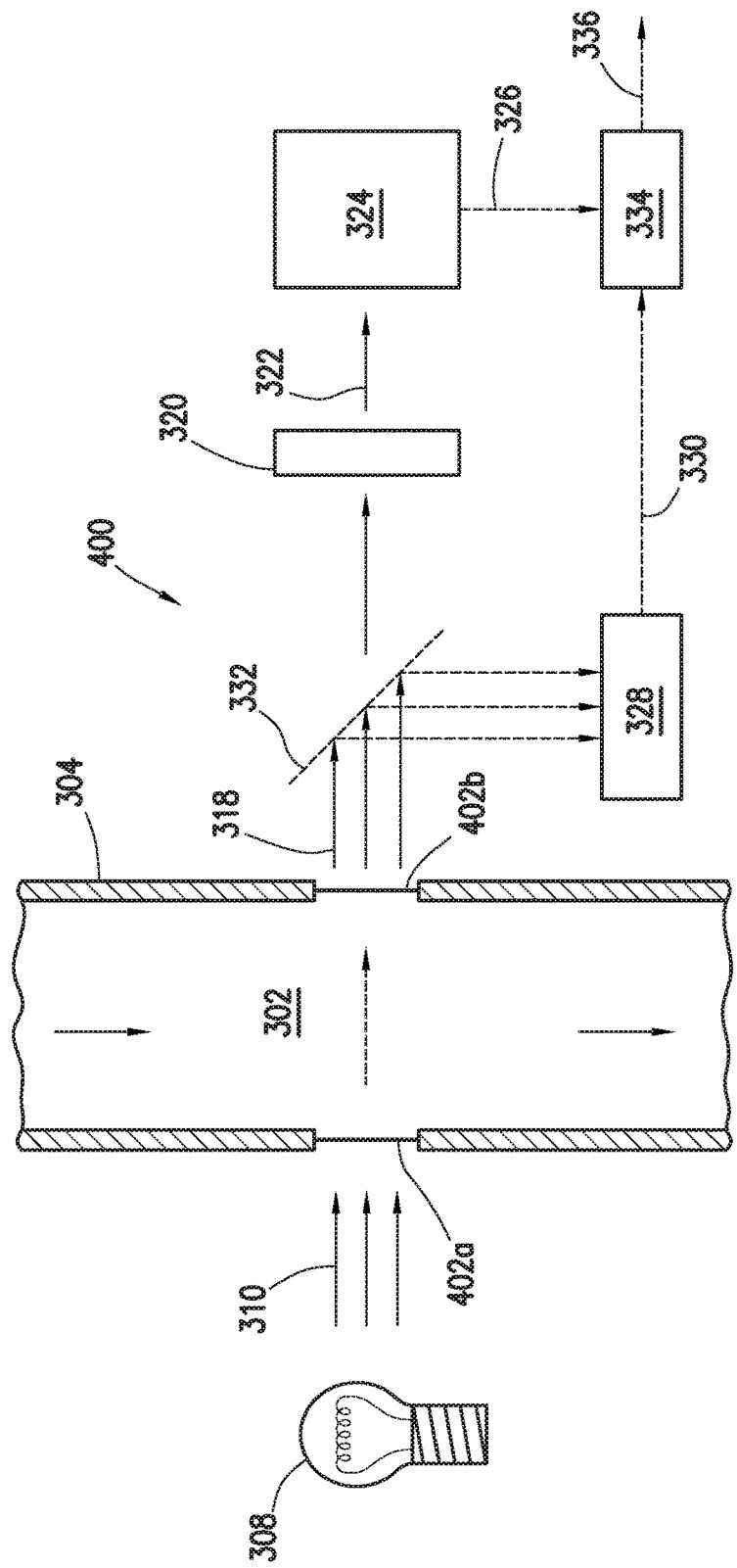
FIG. 9 shows a diagram that illustrates an exemplary optical computing device in which electromagnetic radiation is transmitted through a fluid sample.

Exemplary configurations for the various components of illustrative optical computing devices will now be described in more detail. FIGS. 8 and 9 show diagrams that illustrate exemplary optical computing devices configured for receiving electromagnetic radiation from a sample and processing the electromagnetic radiation using multiple integrated computational elements.

FIG. 8 shows a diagram that illustrates an exemplary optical computing device in which electromagnetic radiation is reflected from a fluid sample. As illustrated in optical computing device 300, fluid 302 may be contained or otherwise flowing within flow path 304. For example, flow path 304 may be a flow line, a pipeline, a wellbore, an annulus defined within a wellbore, or any flow lines or pipelines extending to/from a wellbore. Portions of flow path 304 may be arranged substantially vertically, substantially horizontally, or any directional configuration therebetween.

Optical computing device 300 may include electromagnetic radiation source 308 configured to emit or otherwise generate electromagnetic radiation 310. In some embodiments, lens 312 may collect or otherwise receive electromagnetic radiation 310 and direct electromagnetic radiation beam 314 toward fluid 302. Lens 312 may be any type of optical device configured to transmit or otherwise convey electromagnetic radiation 310 as desired, such as a normal lens, a Fresnel lens, a diffractive optical element, a holographic graphical element, a mirror (e.g., a focusing mirror), or a type of collimator. In some embodiments, lens 312 may be omitted from device 300 and electromagnetic radiation 310 may instead be directed toward fluid 302 directly from electromagnetic radiation source 308.

In some embodiments, optical computing device 300 may also include sampling window 316 arranged adjacent to or otherwise in contact with fluid 302 for detection purposes. Sampling window 316 may be made from a variety of transparent, rigid or semi-rigid materials that are configured to allow transmission of electromagnetic radiation 310 therethrough. For example, sampling window 316 may be made of glasses, plastics, semiconductors, crystalline materials, polycrystalline materials, hot or cold-pressed powders, any combination thereof, and the like. After passing through sampling window 316, electromagnetic radiation 310 optically interacts with fluid 302 and is reflected therefrom.

Electromagnetic radiation 318 generated by the interaction with fluid 302 may be directed to or otherwise be received by integrated computational elements 320. Integrated computational elements 320 may comprise multiple sequenced integrated computational elements from any of the configurations described above. Accordingly, integrated computational elements 320 may be configured to receive electromagnetic radiation 318 and produce modified electromagnetic radiation 322 corresponding to a characteristic of fluid 302.

While FIG. 8 depicts integrated computational elements 320 as receiving reflected electromagnetic radiation from fluid 302, they may alternately be arranged at any point along the optical train of optical computing device 300. For example, in one or more embodiments, integrated computational elements 320 (as shown in dashed) may be arranged within the optical train prior to the sampling window 316. In still other embodiments, integrated computational elements 320 may generate modified electromagnetic radiation 322 through reflection, instead of through transmission.

Modified electromagnetic radiation 322 generated by integrated computational elements 320 may subsequently be conveyed to detector 324 for analysis. In some embodiments, detector 324 may be configured to produce output signal 326 in real-time or near real-time in the form of a voltage (or current) that corresponds to a characteristic of fluid 302. The voltage returned by detector 324 is essentially the dot product of the optical interaction of electromagnetic radiation 318 with integrated computational elements 320 as a function of the magnitude of the characteristic of interest. As such, output signal 326 produced by detector 324 and the magnitude of the characteristic may be related, such as directly proportional, for example. In other embodiments, however, the relationship may correspond to a polynomial function, an exponential function, a logarithmic function, and/or a combination thereof.

In some embodiments, optical computing device 300 may include second detector 328, which may be similar to first detector 324 in that it may be any device capable of detecting electromagnetic radiation. Second detector 328 may be used to detect radiating deviations stemming from electromagnetic radiation source 308. In some embodiments, radiating deviations can occur as a result of a build-up of film or material on sampling window 316, which may have the effect of reducing the amount and quality of electromagnetic radiation ultimately reaching first detector 324. Without proper compensation, such radiating deviations may result in false readings that result in output signal 326 no longer being correlatable with the characteristic of interest.

To compensate for radiating deviations, second detector 328 may be configured to generate compensating signal 330 that is generally indicative of the radiating deviations of electromagnetic radiation source 308, thereby normalizing output signal 326 generated by first detector 324. As illustrated, second detector 328 may be configured to receive a portion of electromagnetic radiation 318 via beamsplitter 332 in order to detect the radiating deviations. In other embodiments, however, second detector 328 may be arranged to receive electromagnetic radiation from any portion of the optical train in optical computing device 300 in order to detect the radiating deviations.

In some embodiments, output signal 326 and compensating signal 330 may be conveyed to or otherwise received by signal processor 334 that is communicably coupled to both of detectors 320 and 328. Signal processor 334 may be a computer including a processor and a machine-readable storage medium having instructions stored thereon, which, when executed by signal processor 334, result in optical computing device 300 performing a number of operations, such as determining a characteristic of interest in fluid 302. Signal processor 334 may utilize an artificial neural network in some embodiments.

In real-time or near real-time, signal processor 334 may provide output signal 336 corresponding to a characteristic of interest in fluid 302. Output signal 336 may be readable by an operator who can consider the results and make proper adjustments or take appropriate action, if needed. In some embodiments, output signal 336 may be conveyed, either wired or wirelessly, to an operator for consideration. In other embodiments, output signal 336 may be recognized by signal processor 334 as being within or outside a predetermined or preprogrammed range of suitable values for operation and may alert an operator in the event of an out-of-range value. In still other embodiments, signal processor 334 may autonomously undertake an appropriate corrective action in order to return output signal 336 to within a desired range.

FIG. 9 shows a diagram that illustrates an exemplary optical computing device in which electromagnetic radiation is transmitted through a fluid sample. Optical computing device 400 may be similar in some respects to optical computing device 300 of FIG. 8, and therefore may be best understood with reference thereto, where like reference characters have been used to enumerate elements having similar functions. Unlike optical computing device 300 of FIG. 8, optical computing device 400 of FIG. 9 may be configured to transmit electromagnetic radiation 310 through fluid 302 via first sampling window 402a and second sampling window 402b arranged radially-opposite first sampling window 402a on flow path 304. First and second sampling windows 402a and 402b may be similar to sampling window 316 described above in regard to FIG. 8 and therefore will not be described in detail again.

As electromagnetic radiation 310 passes through fluid 302 via first and second sampling windows 402a and 402b, it optically interacts with fluid 302, and electromagnetic radiation 318 is subsequently directed to or is otherwise received by integrated computational elements 320. Again, it is to be recognized that integrated computational elements 320 may take the form of any multiple, sequenced integrated computation element configuration described above. Further, it is again to be noted that integrated computational elements 320 may be arranged at any point along the optical train of optical computing device 400. In yet other embodiments, integrated computational elements 320 may generate modified electromagnetic radiation 322 through reflection, instead of through transmission.

Accordingly, methods described herein may comprise: optically interacting incident electromagnetic radiation comprising a plurality of photons sequentially with two or more integrated computational elements, the two or more integrated computational elements being identical to one another and at least a portion of the photons from the incident electromagnetic radiation optically interacting with each integrated computational element; wherein the incident electromagnetic radiation also optically interacts with a sample or is emitted by a sample; and wherein the sequential optical interaction of the incident electromagnetic radiation with the integrated computational elements increases a detection sensitivity relative to that obtained when only one of the integrated computational elements is present; receiving at a detector the photons that have optically interacted with each integrated computational element; and generating an output signal from the detector corresponding to a characteristic of the sample.

In various embodiments, the two or more integrated computational may be disposed in sequence, as described in more detail above. For example, the two or more integrated computational elements may be disposed along a linear optical pathway or a non-linear optical pathway.

In further embodiments, methods of the present disclosure may comprise producing a compensating signal that is not related to the sample or a characteristic thereof, and normalizing the output signal that is related to the characteristic of interest. For example, in more specific embodiments, the compensating signal may account for radiating deviations in the source of electromagnetic radiation, and the output signal may be adjusted to account for the degree of variability in the source of electromagnetic radiation.

Embodiments herein include:

A. Optical computing devices. The optical computing devices comprise: two or more integrated computational elements that are identical to one another and optically interact sequentially with incident electromagnetic radiation comprising a plurality of photons, such that at least a portion of the photons from the incident electromagnetic radiation optically interacts with each integrated computational element; wherein the sequential optical interaction of the incident electromagnetic radiation with the two or more integrated computational elements increases a detection sensitivity of the optical computing device relative to that obtained when only one of the integrated computational elements is present; and a detector that receives the photons that have optically interacted with each integrated computational element.

B. Methods for increasing the sensitivity of an optical computing device. The methods comprise: optically interacting incident electromagnetic radiation comprising a plurality of photons sequentially with two or more integrated computational elements, the two or more integrated computational elements being identical to one another and at least a portion of the photons from the incident electromagnetic radiation optically interacting with each integrated computational element; wherein the incident electromagnetic radiation also optically interacts with a sample or is emitted by a sample; and wherein the sequential optical interaction of the incident electromagnetic radiation with the integrated computational elements increases a detection sensitivity relative to that obtained when only one of the integrated computational elements is present; receiving at a detector the photons that have optically interacted with each integrated computational element; and generating an output signal from the detector corresponding to a characteristic of the sample.

Each of embodiments A and B may have one or more of the following additional elements in any combination:

Element 1: wherein the two or more integrated computational elements are disposed in series with one another along a linear optical pathway.

Element 2: wherein the incident electromagnetic radiation is transmitted through each of the integrated computational elements.

Element 3: wherein the two or more integrated computational elements comprise a monolithic structure.

Element 4: wherein the monolithic structure further comprises an additional neutral optical element.

Element 5: wherein the two or more integrated computational elements are disposed head-to-tail with respect to one another.

Element 6: wherein the two or more integrated computational elements have a combined thickness ranging between about 10 nm and about 1500 nm.

Element 7: wherein the two or more integrated computational elements are disposed in series with one another along a non-linear optical pathway.

Element 8: wherein the incident electromagnetic radiation is reflected from at least a first integrated computational element to a second integrated computational element.

By way of non-limiting example, exemplary combinations applicable to A and B include:

The optical computing device of A or the method of B in combination with elements 1 and 2.

The optical computing device of A or the method of B in combination with elements 2 and 3.

The optical computing device of A or the method of B in combination with elements 1, 2 and 3.

The optical computing device of A or the method of B in combination with elements 1 and 5.

The optical computing device of A or the method of B in combination with elements 1, 3 and 5.

The optical computing device of A or the method of B in combination with elements 3 and 4.

The optical computing device of A or the method of B in combination with elements 7 and 8.

The optical computing device of A or the method of B in combination with elements 5 and 7.

To facilitate a better understanding of the embodiments of the present disclosure, the following examples of preferred or representative embodiments are given. In no way should the following examples be read to limit, or to define, the scope of the disclosure.

EXAMPLES

Example 1

Effect of Placing Integrated Computational Element Design A in Series

Figure 10:
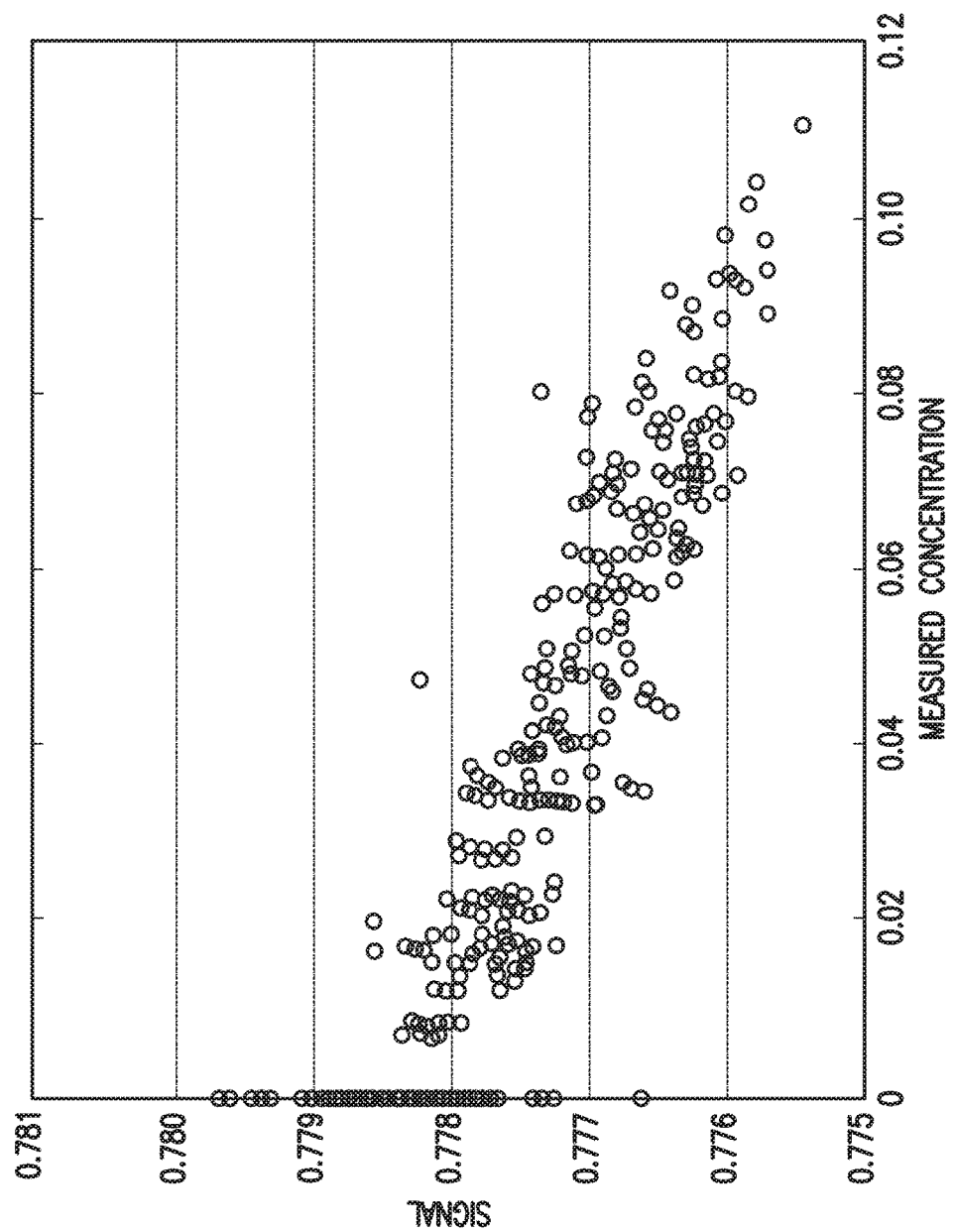
FIG. 10 shows a plot that illustrates modeled signal output as a function of methane concentration for ICE Design A as a single integrated computational element.

An integrated computational element designed for analysis of methane (ICE Design A herein) was modeled in its performance as a function of methane concentration. The estimate of modeled signal output was calculated using the dot product between the transmission profile from an ICE sample spectrum from a training set of data containing spectra of reservoir fluids with varying concentrations of methane and other spectrally interfering components. FIG. 10 shows a plot that illustrates modeled signal output as a function of methane concentration for ICE Design A as a single integrated computational element. Based on the plot of FIG. 10, the relative standard error of calibration (average error in the predicted methane concentration and the measured value from the training set) was 11.33%, and the sensitivity of ICE Design A was determined to be 2.6 V/(g/mL) based upon the slope of the modeled signal output plot.

Figure 11:
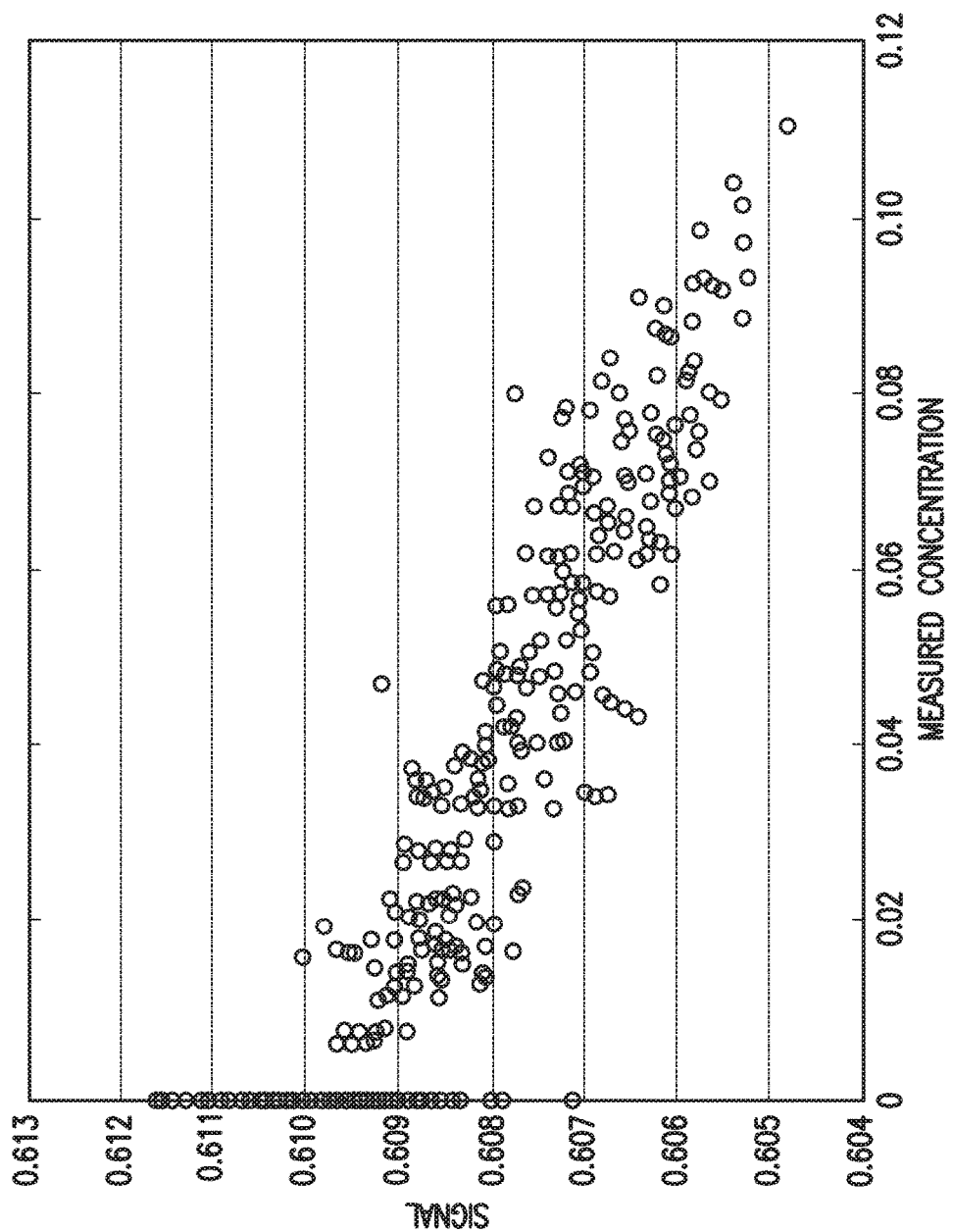
FIG. 11 shows a plot that illustrates modeled signal output as a function of methane concentration for two integrated computational elements of Design A disposed in series with one another.

Modeled signal output for two integrated computational elements of ICE Design A in series was then determined. FIG. 11 shows a plot that illustrates modeled signal output as a function of methane concentration for two integrated computational elements of ICE Design A disposed in series with one another. Based upon the plot of FIG. 11, the relative standard error of calibration was 11.03% and the sensitivity was determined to be 4.4 V/(g/mL) based upon the slope of the modeled signal output plot. Accordingly, significantly increased sensitivity was realized by placing the ICE Design A integrated computational elements in series with one another, while the relative standard error of calibration was relatively unchanged.

The modeled signal output for greater than two integrated computational elements of ICE Design A was then determined. Table 1 below summarizes the relative standard error of calibration and the relative sensitivity change obtained when multiple integrated computational elements of ICE Design A were placed in series with one another.

TABLE 1

| Number of Integrated Computational Elements | Relative Standard Error of Calibration (%) | Relative Change in Sensitivity (%) |
|---|---|---|
| 1 | 11.33 | 0 |
| 2 | 11.03 | 68.8 |
| 3 | 10.89 | 115.2 |
| 4 | 10.93 | 145.2 |
| 5 | 11.10 | 163.0 |
| 6 | 11.39 | 171.8 |

As shown in Table 1, the relative sensitivity increased sharply upon placing two of the integrated computational elements in series, and another significant increase occurred upon placing a third integrated computational element in series. Upon placing further integrated computational elements in series, the relative sensitivity increase was much less pronounced, but still increasing. The performance of ICE Design A against other integrated computational element designs is discussed in more detail below.

Figure 12:
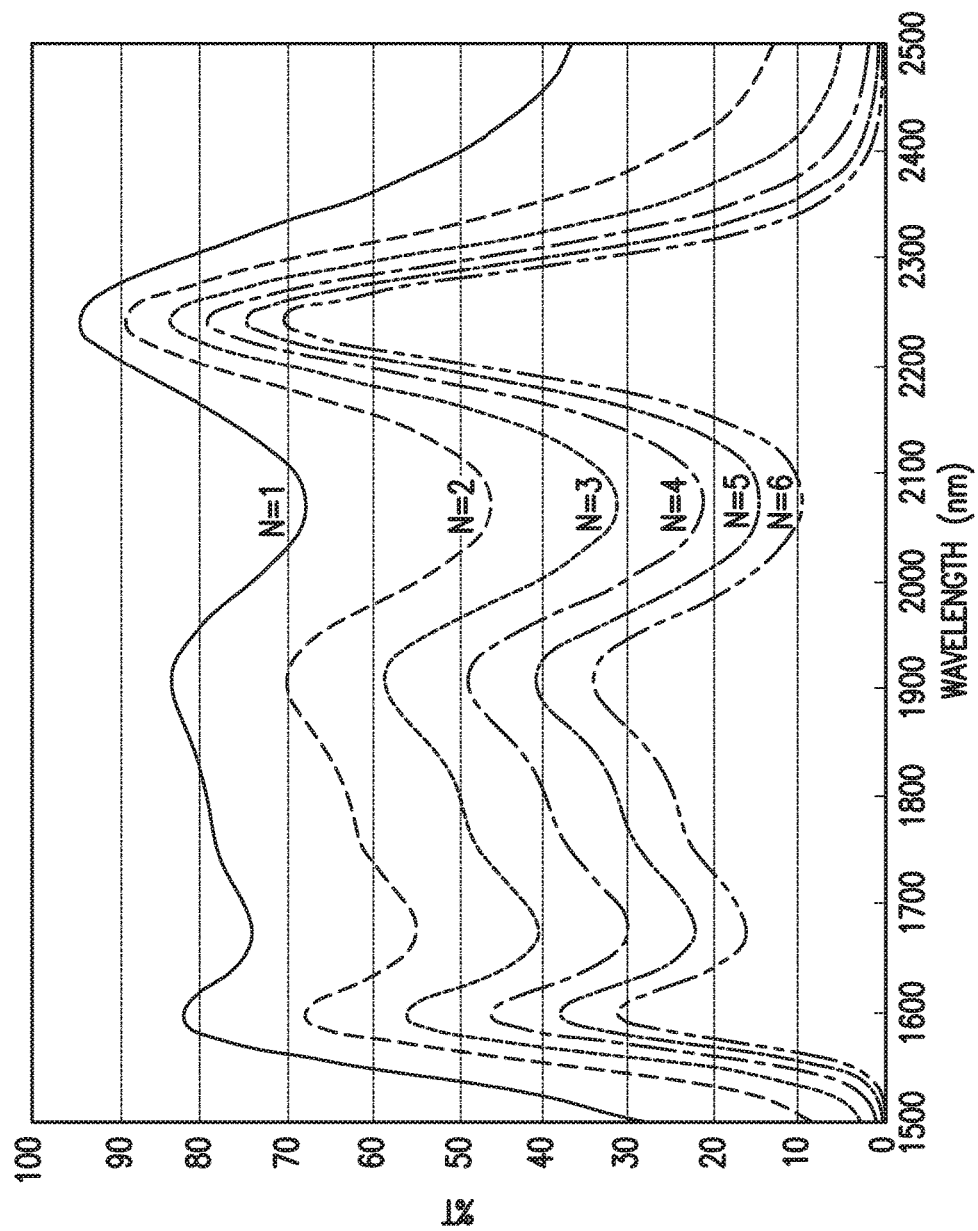
FIG. 12 shows a plot that illustrates simulated transmission intensity as a function of wavelength for ICE Design A, both by itself and when multiply disposed in series.

FIG. 12 shows a plot that illustrates simulated transmission intensity as a function of wavelength for ICE Design A, both by itself and when multiply disposed in series. The transmission plot represents the regression vector for the various configurations of the integrated computational elements. As shown in FIG. 12, the transmission plot became somewhat more complex and the transmission intensity decreased as the number of integrated computational elements was increased. As shown, the decrease in transmission intensity was not uniform across all wavelengths.

Example 2

Comparison of ICE Design A Against Other Integrated Computational Element Designs The performance of ICE Design A was compared against 9 other integrated computational elements also designed for analysis of methane (Designs B-J herein). The performance of ICE Designs B-J were then evaluated singularly and disposed in series with one another, as described above for Example 1. Table 2 below shows the relative standard error of calibration for ICE Designs A-J used singularly and the relative sensitivity change obtained when two ICE Designs A-J were placed in series with one another. For designs B-D, each of which exhibited a sensitivity increase upon placing two of the ICE Designs in series, the calculations were repeated for 3-6 integrated computational elements of like design in series with one another.

TABLE 2

| Integrated Computational Element Design | Number of Integrated Computational Elements | Relative Standard Error of Calibration (%) | Relative Change in Sensitivity (%) |
|---|---|---|---|
| A | 1 | 11.33 | 0 |
| A | 2 | 11.03 | 68.8 |
| A | 3 | 10.89 | 115.2 |
| A | 4 | 10.93 | 145.2 |
| A | 5 | 11.10 | 163.0 |
| A | 6 | 11.39 | 171.8 |
| B | 1 | 11.70 | 0 |

TABLE 2-continued

| Integrated Computational Element Design | Number of Integrated Computational Elements | Relative Standard Error of Calibration (%) | Relative Change in Sensitivity (%) |
|---|---|---|---|
| B | 2 | 11.61 | 30.4 |
| B | 3 | 11.76 | 28.7 |
| B | 4 | 12.20 | 16.9 |
| B | 5 | 12.95 | −4.3 |
| B | 6 | 13.99 | −23.1 |
| C | 1 | 10.86 | 0 |
| C | 2 | 11.21 | 24.3 |
| C | 3 | 12.16 | 17.68 |
| C | 4 | 13.59 | 0.5 |
| C | 5 | 15.29 | −18.5 |
| C | 6 | 17.09 | −35.7 |
| D | 1 | 10.20 | 0 |
| D | 2 | 10.67 | 23.3 |
| D | 3 | 11.91 | 17.3 |
| D | 4 | 13.43 | 1.89 |
| D | 5 | 14.91 | −14.7 |
| D | 6 | 16.24 | −29.8 |
| E | 1 | 10.18 | 0 |
| E | 2 | 10.29 | 31.9 |
| F | 1 | 10.17 | 0 |
| F | 2 | 12.70 | −9.7 |
| G | 1 | 8.22 | 0 |
| G | 2 | 9.16 | −67.0 |
| H | 1 | 8.54 | 0 |
| H | 2 | 12.46 | −41.3 |
| I | 1 | 10.64 | 0 |
| I | 2 | 10.90 | 28.6 |
| J | 1 | 11.00 | 0 |
| J | 2 | 11.21 | 24.6 |

As can be seen in Table 2, ICE Designs A-E, I and J resulted in increased sensitivity when two of the integrated computational elements were combined in series. Unlike ICE Design A, however, Designs B-D did not result in a further sensitivity increase when further integrated computational elements were combined in series.

Figure 13:
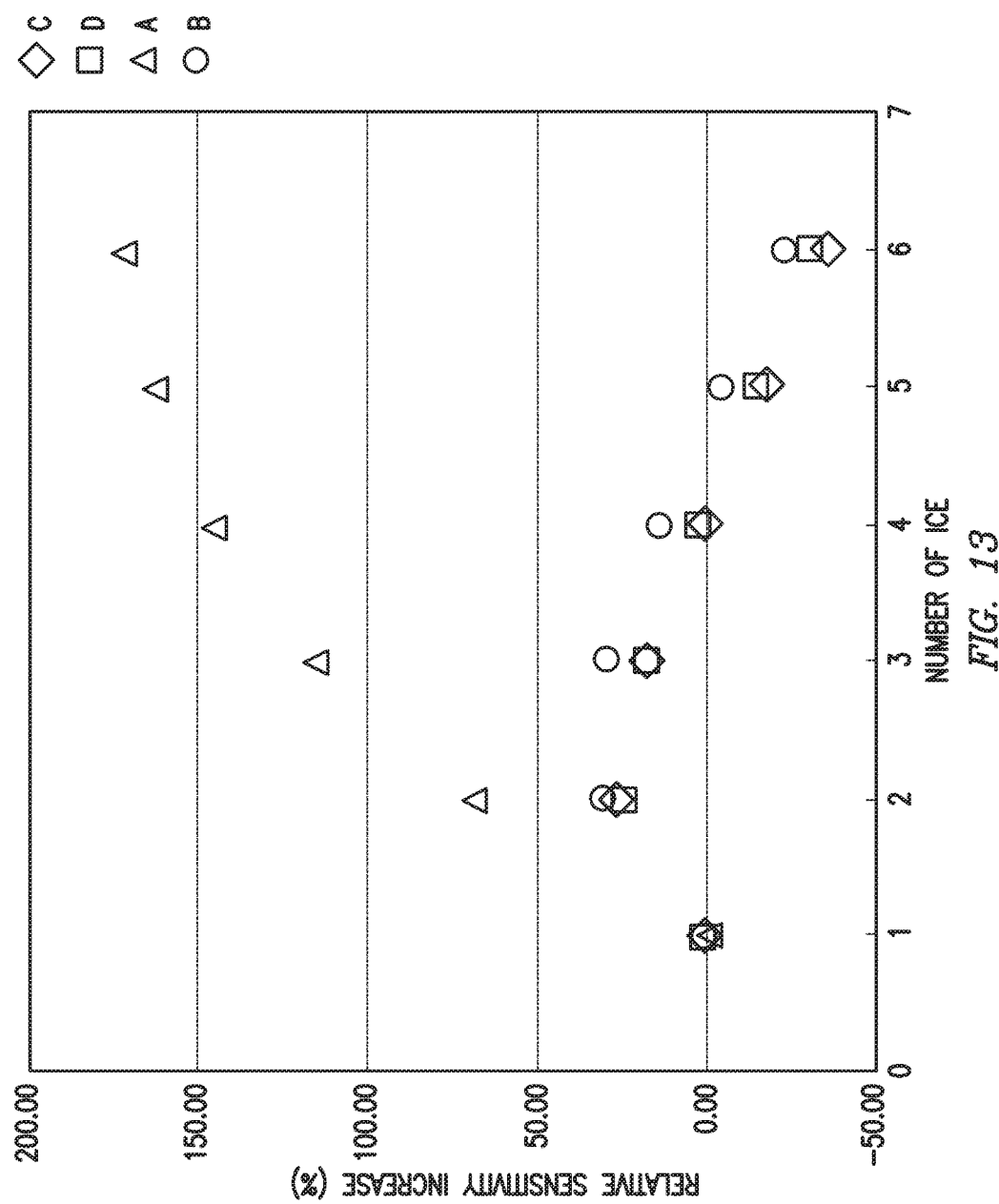
FIG. 13 shows a plot that illustrates the relative sensitivity increase as a function of the number of integrated computational elements disposed in series for ICE Designs A-D.

FIG. 13 shows a plot that illustrates the relative sensitivity increase as a function of the number of integrated computational elements disposed in series for ICE Designs A-D. As shown, ICE Designs B-D displayed optimal performance when 2-3 integrated computational elements were disposed in series, with the best performance being obtained when 2 integrated computational elements were placed in series. In contrast, ICE Design A did not reach a maximum value for the number of integrated computational elements tested, but did appear to be either approaching an asymptotic limit or a true maximum.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An optical computing device comprising:
   two or more integrated computational elements that are identical to one another and optically interact sequentially with incident electromagnetic radiation comprising a plurality of photons, such that at least a portion of the photons from the incident electromagnetic radiation optically interacts with each integrated computational element;
   wherein a sequential optical interaction of the incident electromagnetic radiation with the two or more integrated computational elements increases a detection sensitivity of the optical computing device relative to that obtained when only one of the integrated computational elements is present, and wherein each of the integrated computational elements comprises multiple alternating layers of materials having different thicknesses configured to provide a signal having an optical intensity proportional to a characteristic of a sample according to a same regression vector; and
   a detector that receives the photons that have optically interacted with each integrated computational element.

2. The optical computing device of claim 1, wherein the two or more integrated computational elements are disposed in series with one another along a linear optical pathway.

3. The optical computing device of claim 2, wherein the incident electromagnetic radiation is transmitted through each of the integrated computational elements.

4. The optical computing device of claim 2, wherein the two or more integrated computational elements comprise a monolithic structure.

5. The optical computing device of claim 4, wherein the monolithic structure further comprises an additional neutral optical element.

6. The optical computing device of claim 4, wherein the two or more integrated computational elements are disposed head-to-tail with respect to one another.

7. The optical computing device of claim 4, wherein the two or more integrated computational elements have a combined thickness ranging between about 10nm and about 7000 nm.

8. The optical computing device of claim 1, wherein the two or more integrated computational elements are disposed in series with one another along a non-linear optical pathway.

9. The optical computing device of claim 8, wherein the incident electromagnetic radiation is reflected from at least a first integrated computational element to a second integrated computational element.

10. A method comprising:
   optically interacting incident electromagnetic radiation comprising a plurality of photons sequentially with two or more integrated computational elements, the two or more integrated computational elements being identical to one another and at least a portion of the photons from an incident electromagnetic radiation optically interacting with each integrated computational element;
   wherein the incident electromagnetic radiation also optically interacts with a sample or is emitted by the sample;
   wherein each of the integrated computational elements comprises multiple alternating layers of materials having different thicknesses configured to provide a signal having an optical intensity proportional to a characteristic of the sample according to a same regression vector; and
   wherein a sequential optical interaction of the incident electromagnetic radiation with the integrated computational elements increases a detection sensitivity relative to that obtained when only one of the integrated computational elements is present;
   receiving at a detector the photons that have optically interacted with each integrated computational element; and
   generating an output signal from the detector corresponding to a characteristic of the sample.

11. The method of claim 10, wherein the two or more integrated computational elements are disposed in series with one another along a linear optical pathway.

12. The method of claim 11, wherein the incident electromagnetic radiation is transmitted through each of the integrated computational elements.

13. The method of claim 11, wherein the two or more integrated computational elements comprise a monolithic structure.

14. The method of claim 13, wherein the monolithic structure further comprises an additional neutral optical element.

15. The method of claim 13, wherein the two or more integrated computational elements have a combined thickness ranging between about 10 nm and about 7000 nm.

16. The method of claim 10, wherein the two or more integrated computational elements are disposed in series with one another along a non-linear optical pathway.

17. The method of claim 16, wherein the incident electromagnetic radiation is reflected from at least a first integrated computational element to a second integrated computational element.

18. The method of claim 13, wherein the two or more integrated computational elements are disposed head-to-tail with respect to one another.

* * * * *